United States Patent
Goodfellow et al.

[11] Patent Number: 5,871,542
[45] Date of Patent: Feb. 16, 1999

[54] ENDOPROSTHETIC KNEE JOINT DEVICE

[75] Inventors: John William Goodfellow, Summertown; John Joseph O'Connor, Quarry Manor, both of England

[73] Assignee: British Technology Group Limited, London, England

[21] Appl. No.: 777,794

[22] Filed: Dec. 31, 1996

Related U.S. Application Data

[63] Continuation of PCT/GB95/01594 Jul. 6, 1995.

[30]    Foreign Application Priority Data

Jul. 6, 1994 [GB]  United Kingdom ............ 9413607

[51] Int. Cl.$^6$ ...................................................... A61F 2/38
[52] U.S. Cl. ............................................................. 623/20
[58] Field of Search .................................. 623/16, 18, 20

[56]    References Cited

U.S. PATENT DOCUMENTS

| | | |
|---|---|---|
| 4,224,696 | 9/1980 | Murray et al. . |
| 4,586,933 | 5/1986 | Shojl et al. ............................ 623/20 |
| 4,838,891 | 6/1989 | Branemark et al. ................... 623/20 |
| 5,064,437 | 11/1991 | Stock et al. . |
| 5,092,895 | 3/1992 | Albrektsson et al. ................. 623/20 |

FOREIGN PATENT DOCUMENTS

| | | |
|---|---|---|
| 442 330 | 8/1991 | European Pat. Off. . |
| 2 676 916 | 12/1992 | European Pat. Off. . |
| 1534263 | 11/1978 | United Kingdom . |

*Primary Examiner*—David Isabella
*Attorney, Agent, or Firm*—Cushman Darby & Cushman Intellectual Property Group of Pillsbury Madison & Sutro, LLP

[57]    ABSTRACT

The invention concerns endoprosthetic knee joint devices of the so called 'meniscal knee' variety.

A device is provided of the above type wherein the mutually engaging bearing surfaces of the tibial platform and the meniscal component have a part-cylindrical shaping to allow rotation therebetween about an antero-posterior axis, the superior bearing surface of the tibial platform preferably being convex.

Movements of the natural joint can still be closely simulated and full congruency can be retained throughout the natural range of movement, but there is an additional degree of restraint at the tibio-meniscal interface. Unrestricted antero-posterior relative movement is allowed, as in the conventional meniscal knee, but the part-cylindrical interface shaping serves to reduce the risk of lateral or medial dislocation.

6 Claims, 1 Drawing Sheet

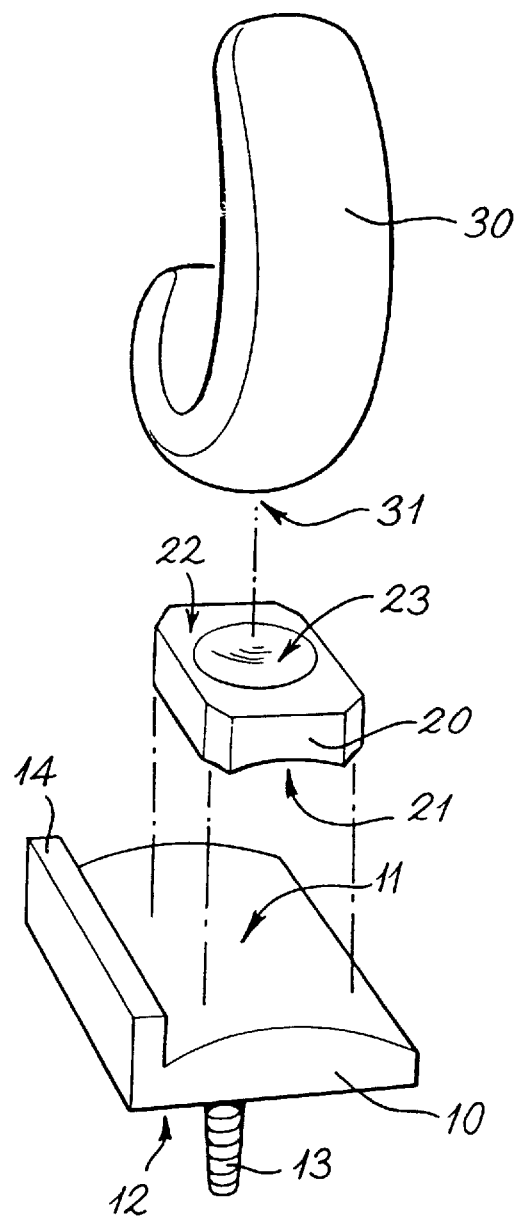

ENDOPROSTHETIC KNEE JOINT DEVICE

This is a continuation of International Application Ser. No. PCT/GB95/01594 file Jul. 6, 1995 which designated the U.S.

The invention concerns endoprosthetic knee joint devices.

Considerable development has taken place in recent decades with regard to knee joint replacement. A significant advance in this area has been the introduction of the so called 'meniscal knee' to clinical practice. This device is described in patent specification GB-A-1 534 263, which document is included herein by reference.

The meniscal knee was designed to allow the provision of congruent articulation whilst at the same time, as far as possible, permitting movement with all natural degrees of freedom. This was achieved by the inclusion between a proximal tibial platform and a distal femoral component of a meniscal component having an inferior and a superior articulatory bearing surface. By forming the engaged femoro-meniscal interface as part spherical, and the tibio-meniscal interface as planar, the rotational and translational articulations of the human knee movement can take place without loss of congruency. The surface arthroplasty of such a device is unconstrained, meaning that the respective components are held in engagement only by the related ligamentous structures and the other surrounding soft tissue.

The meniscal knee device may be of uni-, bi- or tricomparttnental form. In the case of a bi- or tricompartnental device the medial and lateral parts of each component can be of twinned or integrated form.

Continuous review of clinical experience with meniscal knee implants has shown that problems can occur, particularly in the case of replacement of the lateral compartment. The success rate of such replacements has been limited, due to the fact that the lateral soft tissues (principally the lateral collateral ligament and the ilio-tibial band) offer less certain resistance to distraction of the joint and therefore to bearing dislocation than do the much less extensible medial structures. On the lateral side, the tendon of the popliteus muscle passes across the postero-lateral corner of the joint. When the joint is replaced, the tendon can act to propel the meniscal bearing towards the intercondylar region where dislocation can occur.

It is therefore desirable to provide a measure of additional restraint to reduce the risk of dislocation, particularly in the lateral compartment, but also in the medial compartment in certain situations. Present meniscal knee joint devices are known which provide such additional restraint at the tibio-meniscal interface with a view to avoiding dislocation of the meniscal component. To this end, tracked designs with dovetail connections and other forms of mechanical captivity for the meniscal component are known. Although reducing risk of dislocation, these designs can introduce undesirable limits to the freedom of movement allowed at the interface. In particular, long axis rotation about a vertical axis, which occurs naturally in association with flexion/extension and which gives rise to a component of movement of the meniscal component(s) in a medio-lateral direction, can be very difficult to adequately accommodate, and such devices can have a tendency to jam in certain circumstances. Where fully tracked designs are appropriate, their use can lead to an unacceptable increase in contact stresses and component wear at both the femoro-meniscal and the tibio-meniscal interfaces. The addition of a securement means to hold the meniscal component captive introduces the risk of high stresses on the meniscal component as it can readily impact on the securement means. The potential result of this is unacceptable wear.

Other designs have been proposed, but it is not believed that any known knee prosthesis device provides an appropriate solution to the problem. One such design is described in patent application FR-A-2 676 916, which proposes a tricompartmental knee prosthesis having two femoral condylar elements (in separate or integrated form), two plastic floating meniscal elements, and a tibial platform with two laterally spaced bearing surfaces inclined towards one another. The inclination of the tibio-meniscal interface is designed to provide a means of limited restraint against lateral dislocation of the meniscal elements. The bearing surfaces of the tibial component may be curved in lateral aspect (ie. about a medio-lateral axis), or may in one possible mode of realisation be spherical.

A major disadvantage of this design resides in the fact that due to the inward inclination of the tibio-meniscal interface, the meniscal components are subject to an inwardly directed force, i.e. a force urging the elements towards the intercondylar zone. With increasing loading, the force increases, and this has the potential to adversely affect the congruency between the femoral condyles and the meniscal components. The inward inclination also has the effect of bringing the femoral components towards one another, thus reducing the intercondylar space available for the residual soft tissue.

Additionally, in long-axis rotation of the joint, wherein one of the femoral condyles moves forward and the other rearward, and the lateral separation between the meniscal components accordingly reduces, the separation between the femoral component and the tibial platform reduces as the meniscal components both move down their respective inclined tibial bearing surface. This reduction in separation is generally undesirable, as the soft tissues will slacken and make dislocation of the meniscal component more likely. The situation is exacerbated yet further in the case of a tibio-meniscal interface curved in lateral aspect (ie. about a medio-lateral axis). Such a curvature is also undesirable because it further increases the distance by which the bones must be separated in order to insert the meniscal component during implantation. This stretches the soft tissues more than would otherwise be necessary and so increases the danger of damage. The design, then, does address at least partly the problem of lateral dislocation, but at some considerable cost to other aspects of performance of the device.

In the case of the suggested spherical shaping for the tibio-meniscal interface, when the femoro-meniscal interface is also spherical the meniscal component will be free to spin about the long axis of the joint. This is an undesirable situation, particularly when there is directionality to the form of the meniscal component, as is generally the case.

Furthermore, the devices proposed in FR-A-2 676 916 are wholly inapplicable in unicompartmental situations and indeed are described only for tricompartmental realisation.

It is an object of the present invention to reduce or obviate the drawbacks of known meniscal knees by providing a device which allows full freedom of movement of the joint and which gives the possibility of congruency over the natural movement range, whilst ensuring a degree of restraint sufficient to reduce the risk of lateral/medial dislocation.

According to the invention, there is provided a prosthetic knee joint comprising: a tibial platform having a superior bearing surface for replacing at least part of the tibial knee facet; a femoral component for replacing at least part of the femoral knee facet, said femoral component having an inferior bearing surface for slidably engaging the superior bearing surface of a meniscal component; and a meniscal component having an inferior bearing surface for slidably engaging the superior bearing surface of the tibial platform, and a superior bearing surface, the meniscal component providing an articulated joint between the tibial platform and the femoral component, wherein the mutually engaging bearing surfaces of the tibial platform and the meniscal component have a part-cylindrical shaping to allow rotation therebetween about an antero-posterior axis.

The device of the invention, then, is able to permit movement of the meniscal component over the surface of the tibial platform in all directions, enabling it to follow the movement of the femoral component whilst ensuring a relatively large area of contact at the tibio-meniscal interface. In addition, it provides the desired degree of restraint in the medio-lateral direction. It is to be noted that the extent of movement of the meniscal component over the tibial platform in flexion/extension of the knee joint is up to 13 mm in the antero-posterior direction (in the lateral compartment), but only about 3 mm in the medio-lateral direction. It is therefore highly advantageous to allow unrestricted antero-posterior movement.

Preferably, the superior bearing surface of the tibial platform is convex, whilst the inferior bearing surface of the meniscal component is concave.

The invention may be realised in a unicompartmental kneejoint prosthesis, in which the tibial platform is adapted to replace only the lateral or the medial portion of the tibial knee facet.

In unicompartmental knee joint disorders the cruciate ligaments are often retained, whilst the unaffected natural compartment provides great stability to the resulting joint. In this situation the device of the present invention is of particular utility, as the meniscal component is free to move whilst still affording resistance to dislocation to a surprisingly high degree.

In a preferred form, the inferior bearing surface of the femoral component has a convex part-spherical shaping, whilst the superior bearing surface of the meniscal component has a complementary part-spherical concave shaping. Such a feature is known per se from, eg. GB-A-1 534 263, but is of particular significance in the context of the present invention in allowing the full range of movement of the joint whilst retaining, as far as possible, congruency between all mutually engaging component surfaces.

The tibial platform may be provided with means for limiting the extent of relative lateral and/or medial movement of the meniscal component, such as an upstanding flange on the intercondylar side of the tibial platform.

By way of illustration, the invention will now be described by way of example, with reference to the accompanying drawing, which depicts a set of components, these being the constituent parts of a unicompartmental prosthetic knee joint device.

In the illustrated set, the tibial, meniscal and femoral components are respectively denoted by reference numerals 10, 20 and 30.

The tibial component 10 is adapted to replace only the lateral or the medial portion of the tibial knee facet and comprises a tibial platform, of which one face 11 defines a convex surface of part-cylindrical shaping to serve as an articulatory bearing surface, whilst the opposite face 12 serves as a fixation surface adapted for securement to the proximal end of the tibia. In the figure, the tibial platform is shown as rectangular in plan, although the corners will in reality be of smooth curved form to match more closely the plan form of the proximal end of the tibia. From face 12 projects at least one fixation stem 13 to aid in the securement of tibial component 10 to the bone. The stem may project from a central position on the tibial component, as shown in the figure. Alternatively, the fixation stem or stems may project from a position closer to the side of the component intended to be directed towards the intercondylar region (nearer the centre of the tibial plateau), in order to reduce the removal of good quality tibial bone from directly below the component.

The meniscal component 20 comprises a rectangular bearing body of generally smaller dimensions than platform 10, one face 21 of which defines a concave surface of part-cylindrical shaping of the same radius of curvature as face 11 of the tibial component to serve as an articulatory bearing surface. The cylindrical surfaces of faces 21 and 11 are therefore complementary and, when engaged, form a fully congruent sliding bearing. The opposite face 22 of the meniscal component features a part-spherical recess 23 to serve as an articulatory bearing surface.

The third component of the set is a femoral component 30 which comprises a bearing body in the general form of a longitudinally curved strip of which the convex face 31 defines a part-spherical surface of the same radius of curvature as recess 23. The part-spherical faces 23 and 31 are therefore complementary and, when engaged, form a fully congruent sliding bearing.

In use of these components the femoral and tibial components are secured to suitably prepared sites in the femur and tibia respectively with the cylindrical axis of the surface of the tibial platform orientated in the antero-posterior direction. The meniscal component is then engaged between the femoral and tibial components as indicated in the drawing. This procedure is, of course, similar to that used in implanting existing unicompartmental components of meniscal form.

A significant improvement of this device over previous meniscal knee devices resides in the fact that, whilst the movements of the natural joint can still be closely simulated and full congruency can be retained throughout the natural range of movement, there is an additional degree of restraint at the tibio-meniscal interface. Unrestricted antero-posterior relative movement is allowed, as in the conventional meniscal knee. In the medio-lateral direction, however, movement of the meniscal component over the tibial platform surface (due, for example, to long-axis rotation about a vertical axis) results in a rotation of the meniscal component about an axis lying in the antero-posterior direction, which, as explained below, serves to reduce the risk of dislocation. In other words, the design accommodates medio-lateral movement at this interface by rotation, without loss of the captivity provided by the cylindrical interface shaping. Moreover, insertion of the meniscal component from the front of the joint is a relatively straightforward matter.

Dislocation in prosthetic knee joints occurs when the gap between the femoral and tibial components opens up against the resistance of the ligamnents sufficiently to allow the meniscal component to pass through. By shaping the meniscal component according to the present invention, the resulting difference in thickness between the thickest and thinnest parts of the meniscal component means that the bones must separate by a greater distance for dislocation to occur in the medial or lateral direction, so increasing the resistance of the device to meniscal dislocation.

Apart from increasing the resistance of the device to dislocation, the use of a curved surface on the tibial component allows greater surgical laxity in the positioning of the femoral component relative to the tibial component in the medio-lateral plane. The meniscal component will be located such that the plane normal to its articulatory surfaces through the thinnest part of the component passes through the centres of curvature of both the femoral and meniscal components. As the surface of the tibial component is convexly curved in medio-lateral aspect, the range within which the centre of curvature of the femoral component can be placed is increased, when compared with a flat or concave tibial component bearing surface.

When considering long axis rotation of the joint, this is accommodated by an antero-posterior sliding of the meniscal component along the tibial platform, a medio-lateral movement of the centre of the meniscal component over the tibial platform, and a complex rotation of the femoral component relative to the meniscal component at the femoro-meniscal interface. The shaped tibial component according to the invention allows more long axis rotation before the meniscal component approaches the intercondylar region of the tibial component, thus reducing in such movement the risk of medio-lateral dislocation, and reducing the risk of damage to residual intercondylar soft tissues.

The meniscal component may be thinner at the back than at the front, having effectively a raised lip to the front of the superior bearing surface. This design makes implantation easier and is especially applicable in the medial compartment, providing enhanced entrapment of the meniscal component against rearward dislocation, by way of the femoro-meniscal interface. Approximate suitable dimensions for such a component for use in adult patients are: length 34 mm; width 26 mm; depth at front 7 mm; at back 3.5 mm; superior (concave) spherical radius 24 mm; inferior (concave) cylindrical radius 30 mm.

The meniscal component can be fabricated from plastics material, such as ultra-high molecular weight polyethylene, whilst the other components can be made of surgically acceptable metal. This choice of materials is well known in presently used meniscal knee devices as it provides very low friction at both bearing surfaces.

It may also be appropriate to provide the tibial component with a raised side wall or flange positioned on the intercondylar side of the component, as indicated at 14 in the drawing, to prevent the meniscal component contacting exposed bone and other tissue.

In the figure, the femoral component 30 and the tibial component 10 are shown in unicompartmental form. In the case of a total knee implant, whereby both the lateral and medial compartments are replaced, the invention may be realised by employing a unicompartmental tibial component 10 for each compartment. Alternatively, the tibial component may be of unitary bicompartmental form having two portions each with a part cylindrical surface, the axes of curvature of the two cylindrical forms being parallel. Similarly, in such an implant, the femoral component may be of twinned unicompartmental form, or may be formed as a bi- or tricompartmental component.

What is claimed is:

1. A prosthetic knee joint comprising:
   a tibial platform having a superior bearing surface for replacing at least part of the tibial knee facet;
   a meniscal component having an inferior bearing surface for slidably engaging the superior bearing surface of the tibial platform, and a superior bearing surface;
   a femoral component for replacing at least part of the femoral knee facet, said femoral component having an inferior bearing surface for slidably engaging the superior bearing surface of the meniscal component;
   the meniscal component providing an articulated joint between the tibial platform and the femoral component, wherein the mutually engaging bearing surfaces of the tibial platform and the meniscal component have a part-cylindrical shaping to allow rotation therebetween about an antero-posterior axis, such that the meniscal component is able to move over the tibial platform in both an antero-posterior direction and a medio-lateral direction while retaining substantially full congruency at the mutually engaging bearing surfaces.

2. A prosthetic knee joint according to claim 1, wherein the superior bearing surface of the tibial platform is convex, while the inferior bearing surface of the meniscal component is concave.

3. A prosthetic knee joint according to any preceding claim, wherein the inferior bearing surface of the femoral component has a convex part spherical shaping, while the superior bearing surface of the meniscal component has a complementary part-spherical concave shaping.

4. A prosthetic knee joint according to claim 1, wherein the tibial platform is provided with means for limiting the extent of at least one of relative lateral movement and relative medial movement of the meniscal component.

5. A prosthetic knee joint according to claim 4, wherein a limiting means comprises an upstanding flange on the intercondylar side of the tibial platform.

6. A prosthetic knee joint according to claim 1 wherein the tibial platform having two laterally spaced superior bearing surfaces of part-cylindrical shaping, each adapted to engage a separate meniscal component, the axes of curvature of the two superior bearing surfaces being substantially parallel.

* * * * *